(12) United States Patent
Huang et al.

(10) Patent No.: US 12,098,947 B2
(45) Date of Patent: Sep. 24, 2024

(54) INFORMATION PROCESSING DEVICE, WEIGHT ESTIMATION DEVICE, WEIGHT ESTIMATION SYSTEM, INFORMATION PROCESSING METHOD, AND STORAGE MEDIUM

(71) Applicant: NEC Corporation, Tokyo (JP)

(72) Inventors: Chenhui Huang, Tokyo (JP); Kenichiro Fukushi, Tokyo (JP)

(73) Assignee: NEC CORPORATION, Tokyo (JP)

( * ) Notice: Subject to any disclaimer, the term of this patent is extended or adjusted under 35 U.S.C. 154(b) by 398 days.

(21) Appl. No.: 17/612,276

(22) PCT Filed: May 29, 2019

(86) PCT No.: PCT/JP2019/021423
§ 371 (c)(1),
(2) Date: Nov. 18, 2021

(87) PCT Pub. No.: WO2020/240752
PCT Pub. Date: Dec. 3, 2020

(65) Prior Publication Data
US 2022/0221330 A1    Jul. 14, 2022

(51) Int. Cl.
*A43B 3/44*    (2022.01)
*G01G 19/44*    (2006.01)
*G01G 19/52*    (2006.01)

(52) U.S. Cl.
CPC .............. *G01G 19/44* (2013.01); *A43B 3/44* (2022.01); *G01G 19/52* (2013.01)

(58) Field of Classification Search
CPC ........... G01G 19/44; G01G 19/52; A43B 3/44
See application file for complete search history.

(56) References Cited

U.S. PATENT DOCUMENTS

| 4,347,903 A | * | 9/1982 | Yano | G01G 23/3707 |
| | | | | 708/445 |
| 5,585,604 A | * | 12/1996 | Holm | G01G 19/035 |
| | | | | 177/133 |
| 5,959,259 A | * | 9/1999 | Beshears | G01G 19/022 |
| | | | | 177/136 |
| 7,537,573 B2 | * | 5/2009 | Horst | A61H 1/0237 |
| | | | | 600/595 |

(Continued)

FOREIGN PATENT DOCUMENTS

| JP | H01-277721 A | 11/1989 |
| JP | H09-257556 A | 10/1997 |

(Continued)

OTHER PUBLICATIONS

JP Office Action for JP Application No. 2021-521670, mailed on Jul. 19, 2022 with English Translation.

(Continued)

*Primary Examiner* — Randy W Gibson
(74) *Attorney, Agent, or Firm* — Sughrue Mion, PLLC

(57) ABSTRACT

Provided is an information processing device including an acquisition unit configured to acquire load information based on a load applied to a load measurement device from a sole of a user and a feature amount extracting unit configured to extract a feature amount indicating weight of the user by time-integrating time series data included in the load information.

10 Claims, 13 Drawing Sheets

(56) References Cited

U.S. PATENT DOCUMENTS

| | | |
|---|---|---|
| 2009/0293319 A1 | 12/2009 | Avni |
| 2010/0211355 A1 | 8/2010 | Horst et al. |
| 2010/0271051 A1 | 10/2010 | Sankai et al. |
| 2012/0209563 A1 | 8/2012 | Takeda et al. |
| 2012/0253234 A1 | 10/2012 | Yang et al. |
| 2017/0268923 A1 | 9/2017 | Yamada et al. |

FOREIGN PATENT DOCUMENTS

| | | |
|---|---|---|
| JP | 2002-253301 A | 9/2002 |
| JP | 2008-139179 A | 6/2008 |
| JP | 2008-250996 A | 10/2008 |
| JP | WO2009/084387 A1 | 5/2011 |
| JP | 2012-165818 A | 9/2012 |
| JP | 2013-113826 A | 6/2013 |
| JP | 2014-001981 A | 1/2014 |
| JP | 6054905 B2 | 12/2016 |
| JP | 2017-009432 A | 1/2017 |
| JP | 2017-167051 A | 9/2017 |
| JP | 2017-207325 A | 11/2017 |

OTHER PUBLICATIONS

International Search Report for PCT Application No. PCT/JP2019/021423, mailed on Aug. 13, 2019.

* cited by examiner

FIG. 11

| EXPLANATORY VARIABLE | | | | RESPONSE VARIABLE |
|---|---|---|---|---|
| S | P1 | P2 | ... | WEIGHT |
| X1 | Y1 | Z1 | ... | W1 |
| X2 | Y2 | Z2 | ... | W2 |
| ⋮ | ⋮ | ⋮ | ⋮ | ⋮ |

INFORMATION PROCESSING DEVICE, WEIGHT ESTIMATION DEVICE, WEIGHT ESTIMATION SYSTEM, INFORMATION PROCESSING METHOD, AND STORAGE MEDIUM

This application is a National Stage Entry of PCT/JP2019/021423 filed on May 29, 2019, the contents of all of which are incorporated herein by reference, in their entirety.

TECHNICAL FIELD

The present invention relates to an information processing device, a weight estimation device, a weight estimation system, an information processing method, and a storage medium.

BACKGROUND ART

Patent Literature 1 discloses a system for measuring weight of a user using a shoe type wearable device. The system calculates the weight using the magnitude of the force detected by the force sensor and the acceleration detected by the acceleration sensor.

CITATION LIST

Patent Literature

PTL 1: Japanese Patent Application Laid-open No. 2017-167051

SUMMARY OF INVENTION

Technical Problem

In the method for measuring the weight as disclosed in Patent Literature 1, further improvement in measurement accuracy is required.

The present invention intends to provide an information processing device, a weight estimation device, a weight estimation system, an information processing method, and a storage medium which can extract a feature amount of weight with high accuracy.

Solution to Problem

According to one example aspect of the invention, provided is an information processing device including an acquisition unit configured to acquire load information based on a load applied to a load measurement device from a sole of a user and a feature amount extracting unit configured to extract a feature amount indicating weight of the user by time-integrating time series data included in the load information.

According to another example aspect of the invention, provided is an information processing method including acquiring load information based on a load applied to a load measurement device from a sole of a user and extracting a feature amount indicating weight of the user by time-integrating time series data included in the load information.

According to another example aspect of the invention, provided is a storage medium storing a program that causes a computer to perform acquiring load information based on a load applied to a load measurement device from a sole of a user and extracting a feature amount indicating weight of the user by time-integrating time series data included in the load information.

Advantageous Effects of Invention

According to the present invention, an information processing device, a weight estimation device, a weight estimation system, an information processing method, and a storage medium which can extract a feature amount of weight with high accuracy can be provided.

BRIEF DESCRIPTION OF DRAWINGS

FIG. 11 is a table schematically illustrating a correspondence relation between a feature amount vector and weight acquired by the training process.

DESCRIPTION OF EMBODIMENTS

Exemplary embodiments of the present invention are described below with reference to the drawings. Throughout the drawings, the same components or corresponding components are labeled with same references, and the description thereof may be omitted or simplified.

First Example Embodiment

A weight estimation system according to the present example embodiment is described. The weight estimation system of the present example embodiment is a system for estimating weight of a walking user. The increasing interest in health has increased interest in monitoring weight changes. In a weight measurement using a general weight scale, since it is necessary to get on a weight scale installed on the ground, there are large restrictions on a measurement location, a measurement time, a measurement frequency, and the like. In contrast, since the weight estimation system of the present example embodiment estimates the weight of the walking user using the wearable device, there is an advantage in that the measurement location, the measurement time, the measurement frequency, and the like are less restricted. Therefore, the weight estimation system of the present example embodiment is suitable for high frequency weight monitoring applications such as grasping changes in weight during a day. The weight estimation system of the present example embodiment may have a function of acquiring a feature included in the walking pattern of the user (gait) in addition to the estimation of the weight.

Figure 1:
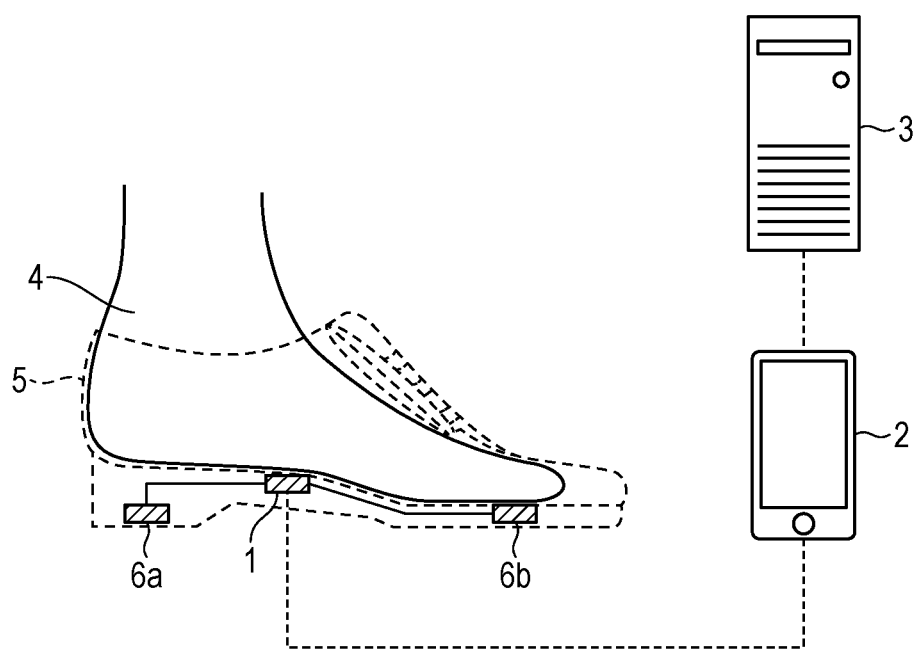
FIG. 1 is a schematic diagram illustrating a general configuration of a weight estimation system according to a first example embodiment.

FIG. 1 is a schematic diagram illustrating a general configuration of a weight estimation system according to the present example embodiment. The weight estimation system includes a weight estimation device 1, an information communication terminal 2, a server 3, and load measurement devices 6a and 6b, which can be connected to each other by wireless communication. The load measurement device 6a may be referred to as a first load measurement device, and the load measurement device 6b may be referred to as a second load measurement device.

The weight estimation device 1 and the load measurement devices 6a and 6b are provided to be close to the sole of a shoe 5 worn by a user 4, for example. The weight estimation device 1 and the load measurement device 6a, and the weight estimation device 1 and the load measurement device 6b are communicatively connected by wiring or the like. The load measurement devices 6a and 6b are sensors for measuring load received from the sole of the user 4. The load measurement devices 6a and 6b convert load received from the user 4 into electrical signals and output the electrical signals to the weight estimation device 1 under the control of the weight estimation device 1. The load conversion method of the load measurement devices 6a and 6b may be a spring type, a piezoelectric element type, a magnetostrictive type, an electrostatic capacitance type, a gyro type, a strain gauge type, or the like, but is not particularly limited. The load measurement devices 6a and 6b are sometimes referred to as load cells. The weight estimation device 1 is an electronic apparatus having a control function of the load measurement devices 6a and 6b, an information processing function of analyzing measured load information, a communication function with the information communication terminal 2, or the like.

Note that, the weight estimation device 1 and load measurement devices 6a and 6b may be provided in the insole of the shoe 5, may be provided in the outsole of the shoe 5, or may be embedded in the shoe 5. The weight estimation device 1 and the load measurement devices 6a and 6b may be detachably attached to the shoe 5 or may be nondetachably fixed to the shoe 5. The weight estimation device 1 and the load measurement devices 6a and 6b may be provided at a portion other than the shoe 5 as long as the weight estimation device 1 can measure the load of the foot. For example, the weight estimation device 1 may be provided in a sock which the user 4 is wearing, provided in a decoration, directly attached to the foot of the user 4, or embedded in the foot of the user 4. Although FIG. 1 illustrates an example in which one weight estimation device 1 and two load measurement devices 6a and 6b are provided on one foot of the user 4, one weight estimation device 1 and two load measurement devices 6a and 6b may be provided on each of both feet of the user 4. In this case, the load information of both feet can be acquired in parallel, and more information can be acquired.

In this specification, the "foot" means a body part below an ankle of the user 4. In addition, in this specification, the "user" means a person who is an object of weight estimation using the weight estimation device 1. Whether or not the user corresponds to the "user" is unrelated to whether or not the user is a user of a device other than the weight estimation device 1 constituting the weight estimation system, whether or not the user receives a service provided by the weight estimation system, or the like.

The information communication terminal 2 is a terminal device carried by the user 4, such as a cellular phone, a smartphone, or a smart watch. Application software for analyzing a walking state is installed in advance in the information communication terminal 2, and processing based on the application software is performed. The information communication terminal 2 acquires data such as an estimation result or the walking state acquired by the weight estimation device 1 and performs information processing using the data. The result of the information processing may be notified to the user 4 or may be transmitted to the server 3. The information communication terminal 2 may have a function of providing software such as a control program of the weight estimation device 1 or a data analysis program to the weight estimation device 1.

The server 3 provides and updates application software for analyzing the walking state to the information communication terminal 2. The server 3 may store data acquired from the information communication terminal 2 and perform information processing using the data.

Note that, the general configuration is an example, and for example, the weight estimation device 1 may be directly connected to the server 3. Further, the weight estimation device 1 and the information communication terminal 2 may be configured as an integrated device, and another device such as an edge server or a relay device may be further included in the weight estimation system.

Figure 2:
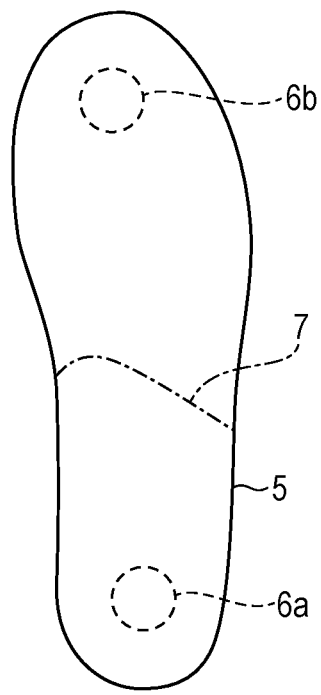
FIG. 2 is a schematic diagram illustrating an arrangement of a weight estimation device according to the first example embodiment.

FIG. 2 is a schematic diagram illustrating an arrangement of load measurement devices 6a and 6b according to the present example embodiment. FIG. 2 is a perspective view of the shoe 5 viewed from the bottom side. The load measurement device 6a is provided at a position corresponding to the heel of the user 4, and the load measurement device 6b is provided between the toe and the load measurement device 6a. More specifically, the load measurement device 6a is provided between the position corresponding to the Lisfranc joint 7 of the foot (the joint between the metatarsal bone and the tarsal bone of the foot) and the heel, and the load measurement device 6b is provided between the position corresponding to the Lisfranc joint 7 of the foot and the toe. A dashed dotted line with reference numeral "7" in the figure indicates the position of the Lisfranc joint 7 when the user 4 wears the shoe 5.

Figure 3:
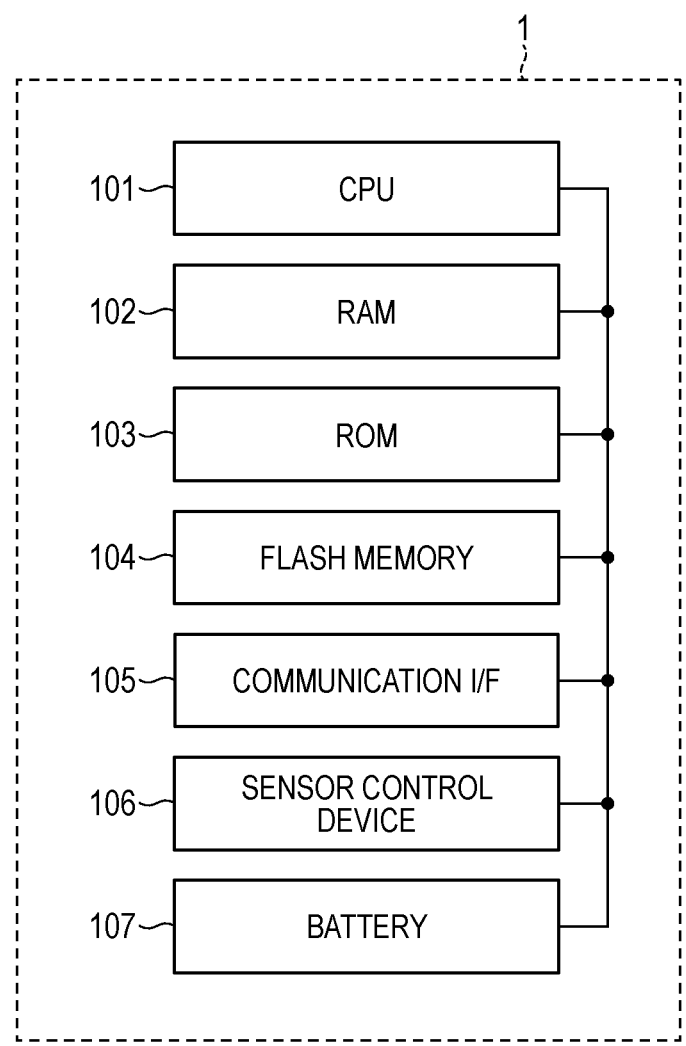
FIG. 3 is a block diagram illustrating a hardware configuration of the weight estimation device according to the first example embodiment.

FIG. 3 is a block diagram illustrating a hardware configuration example of the weight estimation device 1. The weight estimation device 1 is, for example, a microcomputer or a microcontroller. The weight estimation device 1 includes a central processing unit (CPU) 101, a random access memory (RAM) 102, a read only memory (ROM) 103, a flash memory 104, a communication interface (I/F) 105, a sensor control device 106, and a battery 107. Each unit in the weight estimation device 1 is connected each other via a bus, wiring, a driving device, or the like.

The CPU 101 is a processor that performs predetermined calculation in accordance with a program stored in the ROM 103, the flash memory 104, or the like, and also has a function of controlling each unit of the weight estimation device 1. The RAM 102 is composed of a volatile storage medium and provides a temporary memory area required for the operation of the CPU 101. The ROM 103 is composed of a non-volatile storage medium and stores necessary information such as a program used for the operation of the weight estimation device 1. The flash memory 104 is a storage device composed of a non-volatile storage medium and temporarily storing data, storing an operation program of the weight estimation device 1, or the like.

The communication I/F 105 is a communication interface based on standards such as Bluetooth (registered trademark) and Wi-Fi (registered trademark), and is a module for performing communication with the information communication terminal 2.

The sensor control device 106 is a control device that controls the load measurement devices 6a and 6b to measure load and acquires an electric signal indicating the load from the load measurement devices 6a and 6b. The acquired electrical signal is stored in the flash memory 104 as digital data. Thus, the weight estimation device 1 can acquire the load measured by the load measurement devices 6a and 6b as time series data. The load measured by the load measurement device 6a may be referred to as first load information, and the load measured by the load measurement device 6b may be referred to as second load information. The time series data of the load measured by the load measurement device 6a may be referred to as first time series data, and the time series data of the load measured by the load measurement device 6b may be referred to as second time series data. Note that analog-to-digital (AD) conversion for converting analog signals measured by the load measurement devices 6a and 6b into digital data may be performed in the load measurement devices 6a and 6b, or may be performed by the sensor control device 106.

The battery 107 is, for example, a secondary battery, and supplies power necessary for the operations of the weight estimation device 1. When power is required to be supplied to the load measurement devices 6a and 6b, the battery 107 may also supply power to the load measurement devices 6a and 6b. Since the battery 107 is built in the weight estimation device 1, the weight estimation device 1 can operate wirelessly without connecting to an external power source by wire.

Note that the hardware configuration illustrated in FIG. 3 is an example, and other devices may be added or some devices may not be provided. Further, some devices may be replaced by other devices having similar functions. For example, the weight estimation device 1 may further include an input device such as a button so that an operation by the user 4 can be accepted, and may further include an output device such as a display, a display lamp, and a speaker for providing information to the user 4. Thus, the hardware configuration illustrated in FIG. 3 can be changed appropriately.

Figure 4:
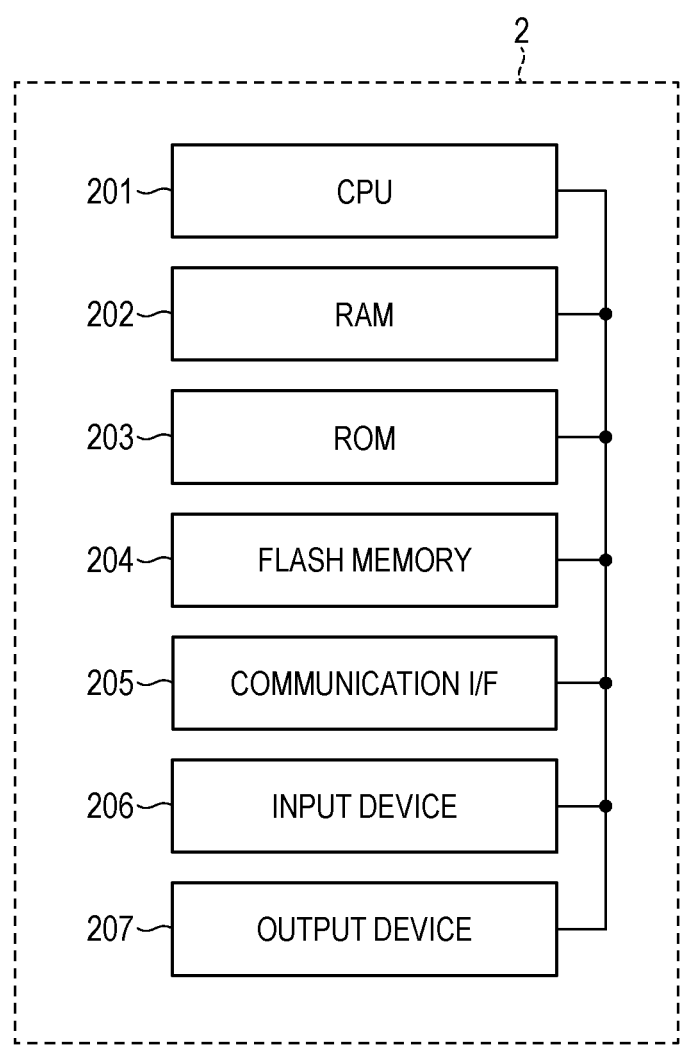
FIG. 4 is a block diagram illustrating a hardware configuration of an information communication terminal according to the first example embodiment.

FIG. 4 is a block diagram illustrating a hardware configuration example of the information communication terminal 2. The information communication terminal 2 includes a CPU 201, a RAM 202, a ROM 203, and a flash memory 204. The information communication terminal 2 also includes a communication I/F 205, an input device 206, and an output device 207. Each unit of the information communication terminal 2 is connected to each other via a bus, wiring, a driving device, or the like.

In FIG. 4, each unit constituting the information communication terminal 2 is illustrated as an integrated device, but some of these functions may be provided by an external device. For example, the input device 206 and the output device 207 may be external devices different from those constituting the functions of the computer including the CPU 201 or the like.

The CPU 201 is a processor that performs predetermined calculation in accordance with a program stored in the ROM 203, the flash memory 204, or the like, and also has a function of controlling each unit of the information communication terminal 2. The RAM 202 is composed of a volatile storage medium and provides a temporary memory area required for the operation of the CPU 201. The ROM 203 is composed of a non-volatile storage medium and stores necessary information such as a program used for the operation of the information communication terminal 2. The flash memory 204 is a storage device composed of a non-volatile storage medium for storing data transmitted and received to and from the weight estimation device 1 and for storing a program for operating the information communication terminal 2.

The communication I/F 205 is a communication interface based on standards such as Bluetooth (registered trademark), Wi-Fi (registered trademark) or 4G and is a module for performing communication with other devices.

The input device 206 is a user interface used by the user 4 to operate the information communication terminal 2. Examples of the input device 206 include a mouse, a trackball, a touch panel, a pen tablet, a button, or the like.

The output device 207 is, for example, a display device. The display device is a liquid crystal display, an organic light emitting diode (OLED) display, or the like, and is used for displaying information, displaying a graphical user interface (GUI) for operation input, or the like. The input device 206 and the output device 207 may be integrally formed as a touch panel.

Note that the hardware configuration illustrated in FIG. 4 is an example, and other devices may be added or some devices may not be provided. Further, some devices may be replaced by other devices having similar functions. Further, some functions of the present example embodiment may be provided by other devices via a network, or some functions of the present example embodiment may be realized by being distributed among a plurality of devices. For example, the flash memory 204 may be replaced by a hard disk drive (HDD) or a cloud storage. Thus, the hardware configuration illustrated in FIG. 4 can be changed appropriately.

The server 3 is a computer having substantially the same hardware configuration as that illustrated in FIG. 4. Since the hardware configuration of the server 3 is substantially the same as that of the information communication terminal 2 except that the server 3 may not be portable, a detailed description thereof is omitted.

Figure 5:
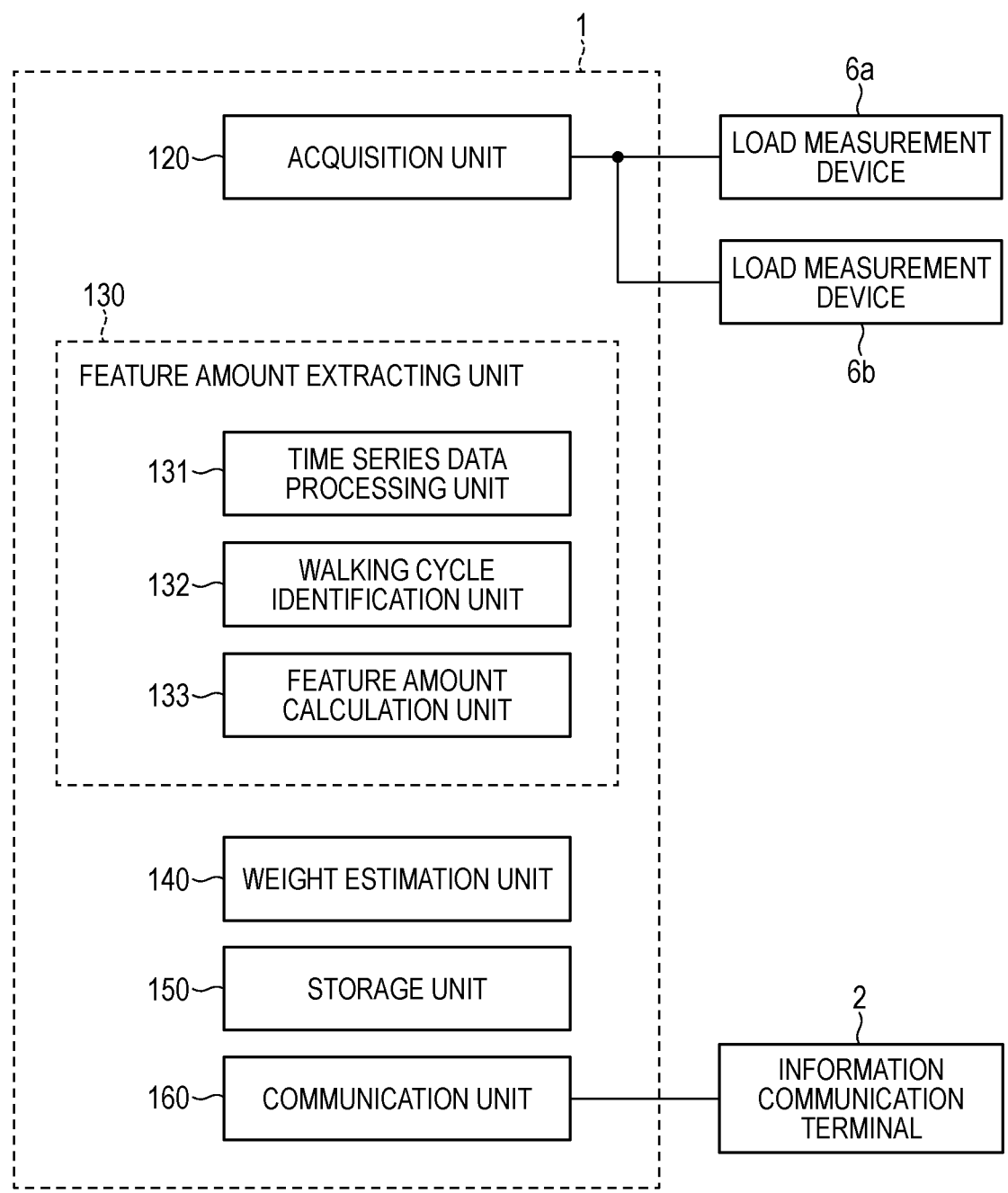
FIG. 5 is a functional block diagram of the weight estimation device according to the first example embodiment.

FIG. 5 is a functional block diagram of the weight estimation device 1 according to the present example embodiment. The weight estimation device 1 includes an acquisition unit 120, a feature amount extracting unit 130, a weight estimation unit 140, a storage unit 150, and a communication unit 160. The feature amount extracting unit 130 includes a time series data processing unit 131, a walking cycle identification unit 132, and a feature amount calculation unit 133.

The CPU 101 loads a program stored in the ROM 103, the flash memory 104, or the like into the RAM 102 and executes the program. Thus, the CPU 101 realizes the functions of the feature amount extracting unit 130 and the weight estimation unit 140. Further, the CPU 101 realizes the function of the acquisition unit 120 by controlling the sensor control device 106 based on the program. The CPU 101 realizes the function of the storage unit 150 by controlling the flash memory 104 based on the program. Further, the CPU 101 realizes the function of the communication unit 160 by controlling the communication I/F 105 based on the program. Specific processing performed by each of these units is described later.

In the present example embodiment, each function of the functional blocks illustrated in FIG. 5 is provided in the weight estimation device 1, but some functions of the functional blocks illustrated in FIG. 5 may be provided in the information communication terminal 2 or the server 3. That is, the above-described functions may be realized by any of the weight estimation device 1, the information communication terminal 2, and the server 3, or may be realized by cooperation of the weight estimation device 1, the information communication terminal 2, and the server 3.

Figure 6:
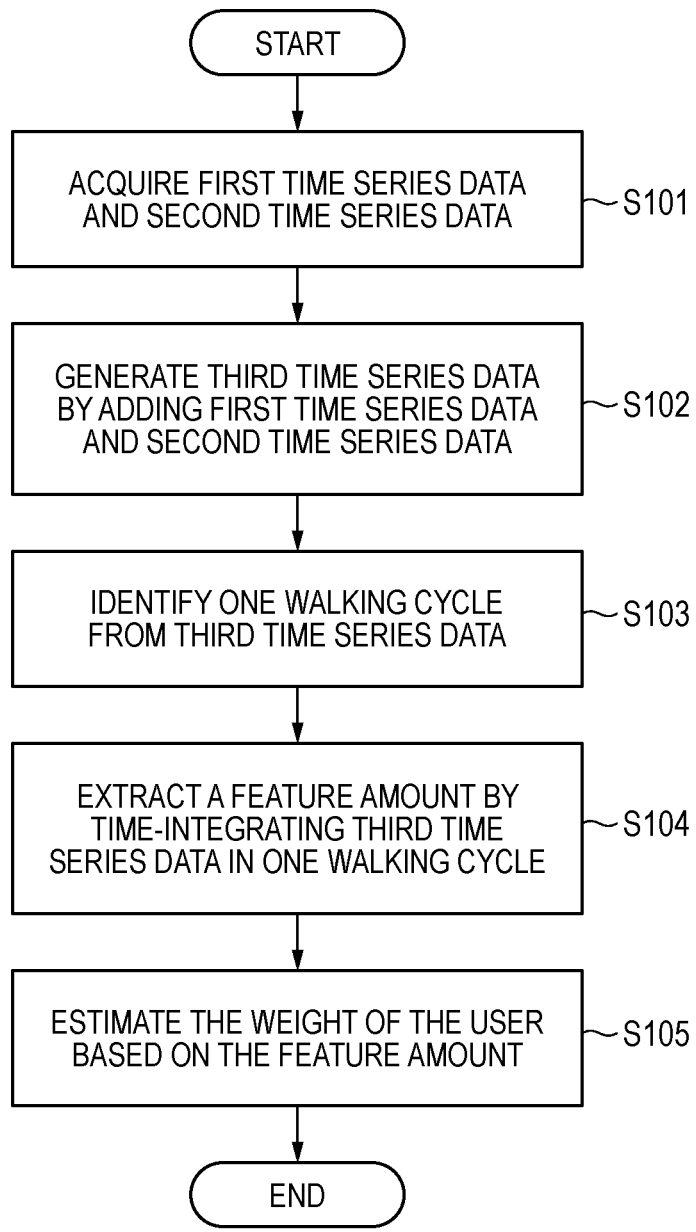
FIG. 6 is a flowchart illustrating an example of weight estimation process performed by the weight estimation device according to the first example embodiment.

FIG. 6 is a flowchart illustrating an example of weight estimation processing performed by the weight estimation device 1 according to the present example embodiment. The process of FIG. 6 is performed when the weight estimation device 1 detects walking of the user 4, for example. Alternatively, the process of FIG. 6 may be always performed unrelated to whether or not the user 4 is walking, or may be performed at predetermined time intervals.

In step S101, the acquisition unit 120 controls the load measurement devices 6a and 6b to acquire time series data of load from each of the load measurement devices 6a and 6b. That is, the acquisition unit 120 acquires the first time series data from the load measurement device 6a and acquires the second time series data from the load measurement device 6b. Thus, the acquisition unit 120 can acquire time changes in the load caused by walking of the user 4. The acquired time series data of the load is converted into digital data and then stored in the storage unit 150. In addition, the time series data of the load is referred to as load information because it indicates the time change of the load. The load information can be used not only for the weight estimation processing of the present example embodiment but also for the gait analysis or personal identification of the user 4.

Figure 7:
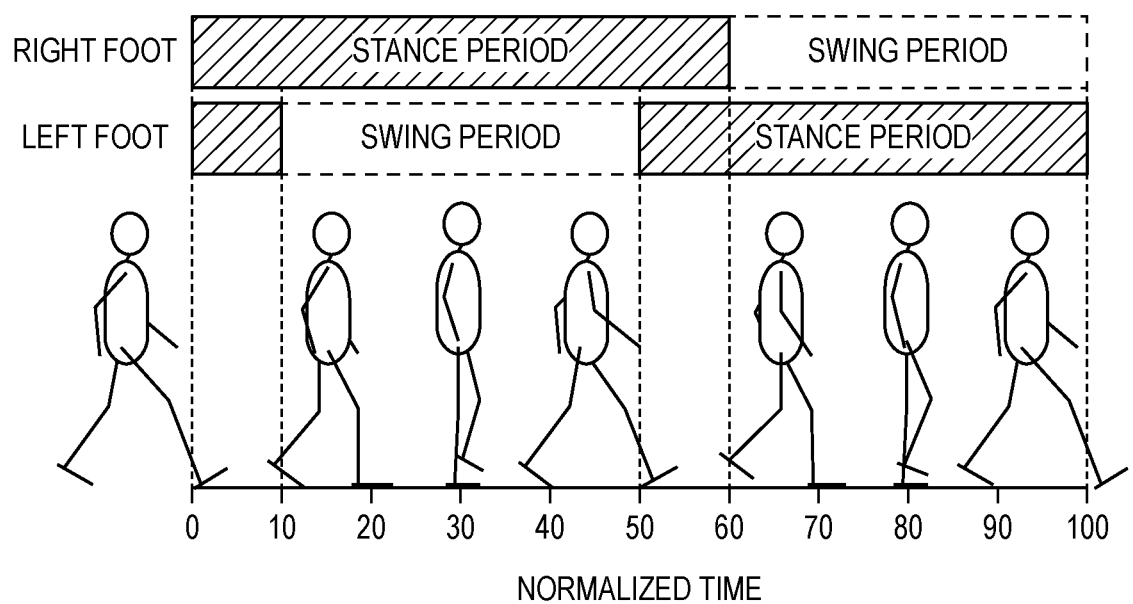
FIG. 7 is a conceptual diagram illustrating a walking cycle.

Here, in order to sufficiently acquire features indicating the weight of the user 4, it is desirable that time series data of the load include data in a period corresponding to at least one walking cycle. One walking cycle is described with reference to FIG. 7. FIG. 7 is a conceptual diagram illustrating a walking cycle. FIG. 7 schematically illustrates motion of the right foot and the left foot of the user 4 for one walking cycle. The normalized time in the figure indicates the time normalized so that the length of one walking cycle is 100. That is, the normalized time 0 in the figure is the moment at which the right foot lands, the normalized time 50 in the figure is the moment at which the left foot lands, and the normalized time 100 in the figure is the moment at which the right foot lands again. A period from the normalized time 0 to 100 is one walking cycle.

Further, a period in which the foot lands is referred to as a stance period, and a period in which the foot leaves the ground is referred to as a swing period. More specifically, for example, the stance period of the right foot is a period from the moment at which the heel of the right foot lands (at the time of landing) to the moment at which the toe of the right foot leaves the ground (at the time of leaving), and generally occupies a period of about 60% of one walking cycle. The swing period of the right foot is a period from the moment when the toe of the right foot leaves the ground to the moment when the heel of the right foot lands, and generally occupies a period of about 40% of one walking cycle. As illustrated in FIG. 7, during walking, the stance period and the swing period are alternately repeated. Further, the phase of the stance period and the phase of the swing period are opposite between the right foot and the left foot.

In step S102, the time series data processing unit 131 generates third time series data by adding the first time series data acquired from the load measurement device 6a and the second time series data acquired from the load measurement device 6b. In this process, digital data of load at the same time in the first time series data and the second time series data is added together. Thus, the third time series data including the feature based on the load output from both the load measurement devices 6a and 6b can be acquired.

The order and contents of step S101 and step S102 can be changed appropriately. Step S101 and step S102 may be performed simultaneously or as a series of processes. For example, when the time series data are acquired from the load measurement devices 6a and 6b, these processes may be modified to a process in which the time series data are added together to generate and store the third time series data. In this case, the first time series data and the second time series data are not necessary to be stored. These processes may be modified to a process of adding analog signals measured by the load measurement devices 6a and 6b in a circuit before AD conversion. In this case, the addition is completed before the acquisition unit 120 acquires the data. In this case, the number of AD conversion processes is reduced.

In step S103, the walking cycle identification unit 132 identifies one walking cycle of the third time series data. Since substantially the same motion is repeated for each step during walking, one walking cycle can be identified by detecting periodicity of the third time series data. For example, one walking cycle can be identified based on the appearance time of the peak or dip of the third time series data, the frequency of the peak included in the frequency spectrum acquired by Fourier-transforming the third time series data, or the like.

In step S104, the feature amount calculation unit 133 extracts a feature amount indicating the weight of the user 4 by time-integrating the third time series data in at least one walking cycle. The extracted feature amount is stored in the storage unit 150. The extraction of the feature amount is described with a specific example.

Figure 8:
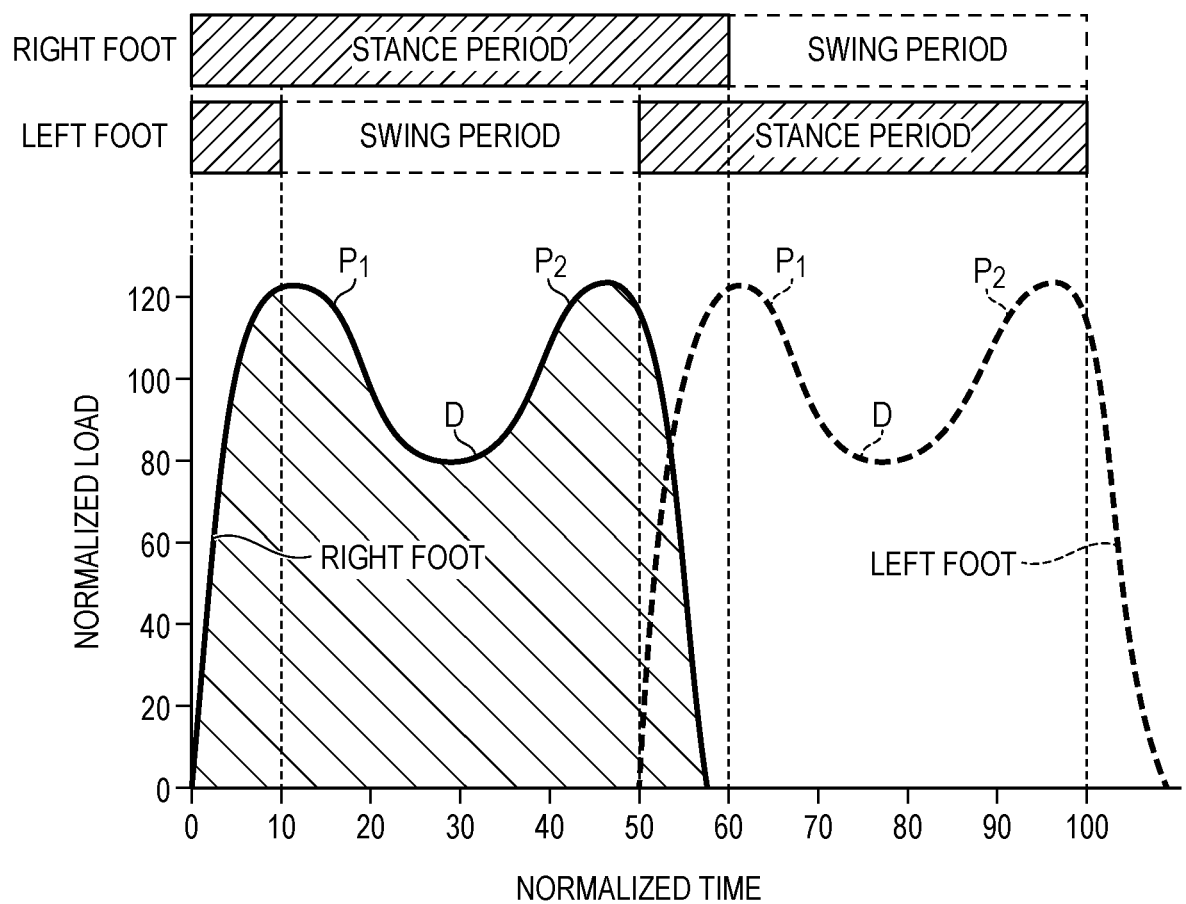
FIG. 8 is a graph illustrating an example of time series data of the load.

FIG. 8 is a graph illustrating an example of the third time series data of load acquired in one walking cycle. The horizontal axis of FIG. 8 represents the normalized time in one walking cycle, and the vertical axis of FIG. 8 represents a value acquired by normalizing the load by the weight (percentage of the load with respect to the weight).

In FIG. 8, the solid line graph illustrates time changes of the load applied to the load measurement devices 6a and 6b from the right foot of the user 4, and the broken line graph illustrates time changes of the load applied to the load measurement devices 6a and 6b from the left foot of the user 4. "P1" and "P2" in the graph indicate peaks in load fluctuation, and "D" in the graph indicates dips in load fluctuation.

The feature amount calculation unit 133 integrates the normalized load of the third time series data in the normalized time. This integral value corresponds to the area of the hatched portion illustrated in the graph of the right foot in FIG. 8. This integral value is stored in the storage unit 150 as a feature amount.

Since an irregular body motion occurs during walking, noise may be large and sufficient accuracy may not be acquired in a case where the weight is estimated from only the instantaneous value of the load. However, humans tend to walk so that the average of body motions in one walking cycle is as small as possible in order to maintain stability of the center of gravity during walking. That is, even though irregular body motion as a noise source instantaneously occurs during walking, noise of irregular body motion can be reduced by integrating data of a time which is long to some extent to extract features (for example, one walking cycle). Therefore, in the present example embodiment, the feature amount calculation unit 133 can extract a feature amount capable of highly accurate weight estimation by time-integrating time series data within one walking cycle and acquiring the integral value as a feature amount.

Note that the feature amount acquired by the feature amount calculation unit 133 is not limited to the integral value described above, and for example, the appearance time of the peak, the size of the peak, the appearance time of the dip, the size of the dip, and the like may be further acquired as the feature amount. As described above, the feature amount extracted in this process may include a plurality of elements, and in other words, the feature amount extracted in this process may be a feature amount vector.

In step S105, the weight estimation unit 140 estimates the weight of the user 4 based on the extracted feature amount. The acquired weight is stored in the storage unit 150. In this case, the weight may be stored in the storage unit 150 in association with the acquisition time.

In the process of estimating the weight performed by the weight estimation unit 140, a trained model generated in advance by machine learning and stored in the storage unit 150 is used. Examples of algorithms used for machine learning include decision trees, random forests, support vector machines, neural networks, deep learning, logistic regression, k-nearest neighbor algorithm (K-NN), ensemble learning for classification method, discriminant analysis, or the like. Further, generation of a trained model by machine learning (training process) is performed in the weight estimation device 1, the information communication terminal 2, or the server 3 using sample data prepared in advance.

The training process for generating a trained model used for personal identification in step S105 is described in more detail. This process is performed in advance in the weight estimation device 1, the information communication terminal 2, or the server 3 prior to the process of FIG. 6. In the description of the present example embodiment, it is assumed that the training process is performed in the server 3.

Figure 9:
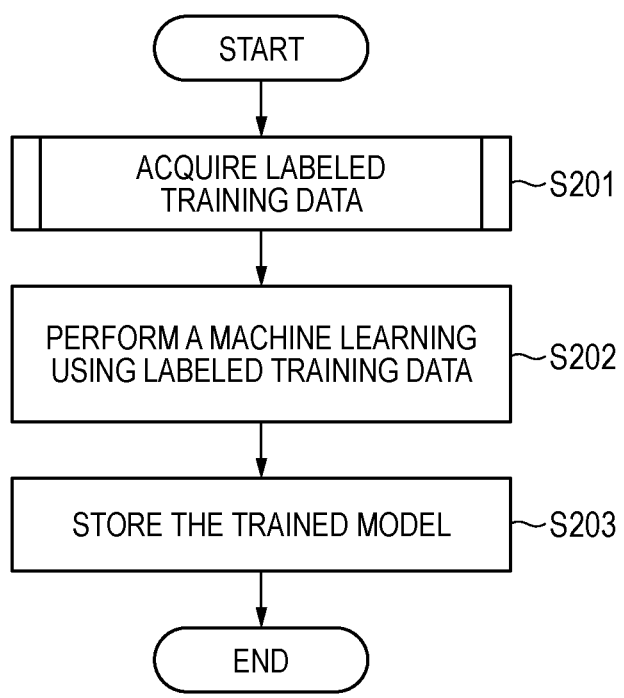
FIG. 9 is a flowchart illustrating an example of training process performed by the server according to the first example embodiment.

FIG. 9 is a flowchart illustrating an example of training process performed by the server 3 according to the present example embodiment. The process of FIG. 9 is performed prior to the weight estimation process at the time of developing the weight estimation system, manufacturing the weight estimation system, or calibration before the user 4 uses the weight estimation device 1, or the like.

Figure 10:
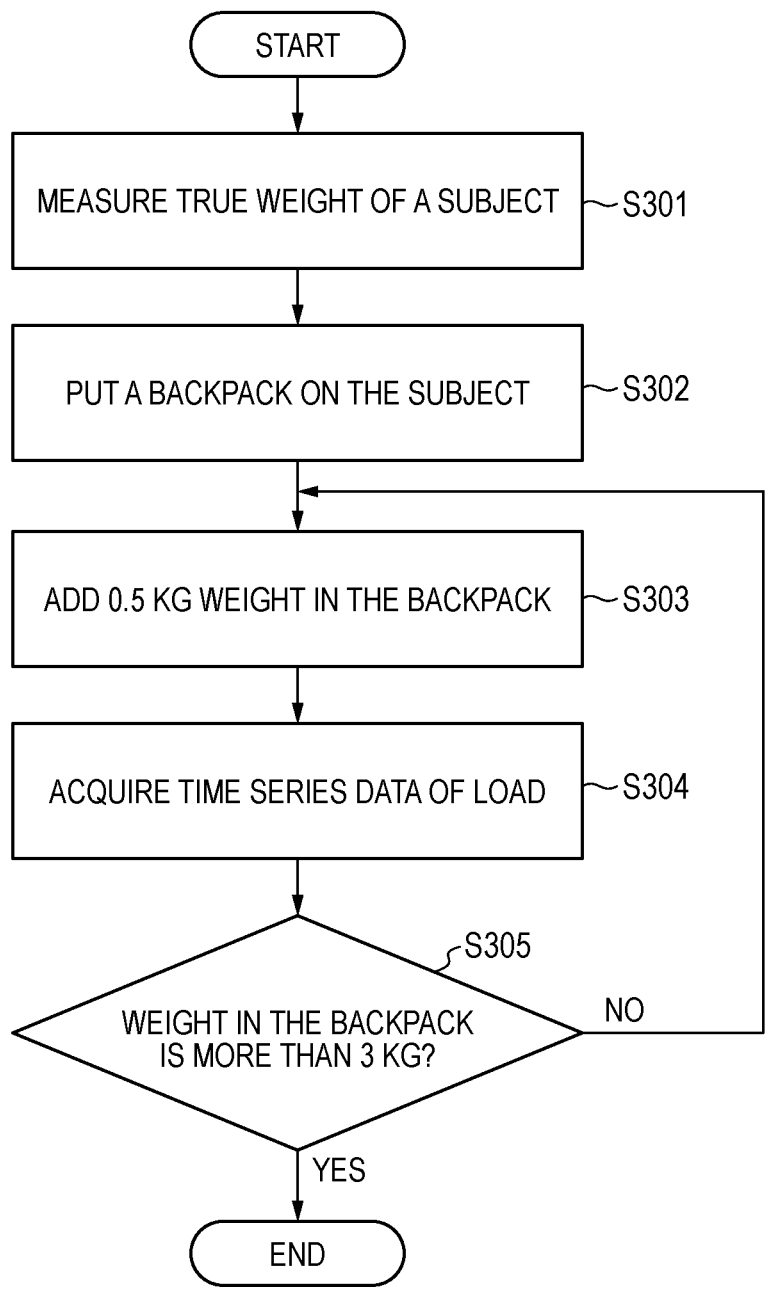
FIG. 10 is a flowchart illustrating an example of a method of generating labeled training data.

In step S201, the server 3 acquires labeled training data prepared in advance. An example of a method of generating this labeled training data is described with reference to FIG. 10. FIG. 10 is a flowchart illustrating an example of a method of acquiring labeled training data. This process is performed by, for example, a labeled training data creator who creates labeled training data and a subject wearing the weight estimation device 1.

In step S301, the labeled training data creator measures the true value of the weight of the subject. This process may be performed, for example, by placing the subject on an appropriately calibrated weight scale and measuring the weight with the weight scale.

In step S302, the labeled training data creator puts the backpack on the subject. By putting a weight in the backpack, the weight of the backpack can be changed in multiple stages. In the initial state, the content of the backpack is empty.

In step S303, the labeled training data creator puts a weight of 0.5 kg in the backpack. In step S304, the subject walks a predetermined distance. At this time, the weight estimation device 1 acquires time series data of the load.

In step S305 after acquisition of the time series data, when the weight in the backpack is 3 kg or more (YES in step S305), acquisition of the labeled training data is ended. When the weight in the backpack is less than 3 kg (NO in step S305), the process proceeds to step S303. That is, the time series data of the load is acquired again by changing the weight of the backpack.

In this way, a plurality of kinds of time series data in which the total weight of the subject (true value of weight of the subject+weight of the backpack) is changed in various ways are acquired. The data group in which the feature amount vector acquired from the time series data is associated with the total weight of the subject is used as the labeled training data in step S201.

In step S202, the server 3 performs machine learning using the labeled training data. As a result, a trained model is generated in which an appropriate weight is output with respect to the input of the feature amount vector.

In step S203, the server 3 stores the trained model in the storage device. Thereafter, the server 3 provides the trained model to the weight estimation device 1. Specifically, the server 3 transmits the trained model to the information communication terminal 2. The information communication terminal 2 causes the weight estimation device 1 to install the received trained model as software for processing in the weight estimation unit 140.

FIG. 11 is a table schematically illustrating a correspondence relation between a feature amount vector and weight acquired by the training process. In FIG. 11, the explanatory variable "S" represents a time integral value of the load. The explanatory variables "P1" and "P2" indicate the first peak time and the second peak time, respectively. As illustrated in FIG. 11, the weight is determined corresponding to a feature amount vector including "S", "P1", "P2", and the like. In other words, the trained model acquired by the training process has a function of outputting weight as a response variable when a feature amount vector is input as an explanatory variable. It should be noted that generation of the trained model by the present training process need not be performed individually for each subject of weight measurement, and the trained model generated for a certain subject may be used for weight estimation of another person.

EXAMPLE

A result of actually performing weight estimation using the weight estimation system of the first example embodiment is described as an example. In the present example, labeled training data were created from ten subjects by the method of FIG. 10, and cross-validation was performed using this labeled training data. Specifically, 15% data randomly selected from the labeled training data were used as validation data, and the remaining 85% data were used as training data. In other words, the training model was generated using the training data of a part of the data group, and the weight was estimated using the remaining data.

Figure 12:
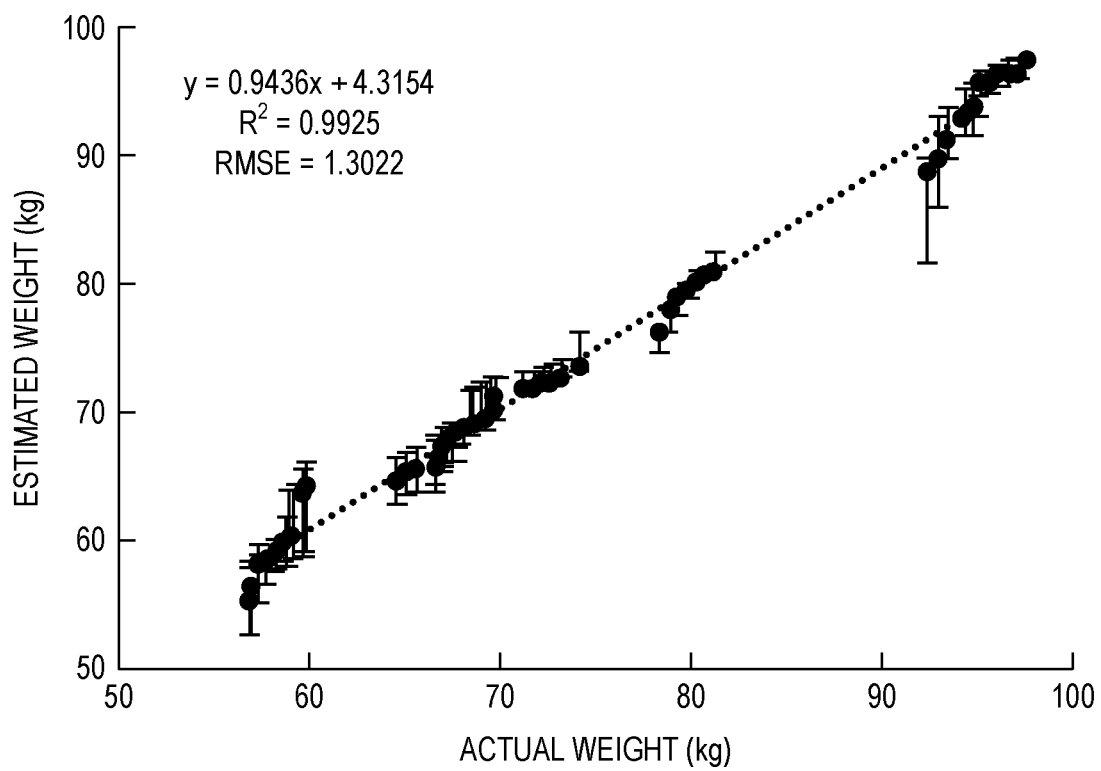
FIG. 12 is a graph illustrating a result of cross-validation.

FIG. 12 is a graph illustrating a result of cross-validation. The horizontal axis of the graph is the actual weight of the subject measured using the weight scale, and the vertical axis of the graph is the weight estimated by the weight estimation system of the present example embodiment. As illustrated in FIG. 12, the value of a root mean squared error (RMSE) was about 1.30 kg, and the value of the coefficient of determination (R2) was 0.99 or more. It was confirmed that an estimation error of 2.5% or less of the weight required for weight monitoring could be achieved, and weight estimation could be performed with sufficient accuracy. As described above, according to the present example embodiment, the weight estimation device 1 and the weight estimation system capable of estimating the weight with high accuracy are provided.

As described above, according to the present example embodiment, the information processing device capable of extracting the feature amount of the weight with high accuracy is provided. In addition, by using the feature amount extracted by the information processing device, the weight estimation device 1 and the weight estimation system which can estimate the weight with high accuracy is provided.

The device or system described in the above example embodiment can also be configured as in the following second example embodiment.

Second Example Embodiment

Figure 13:
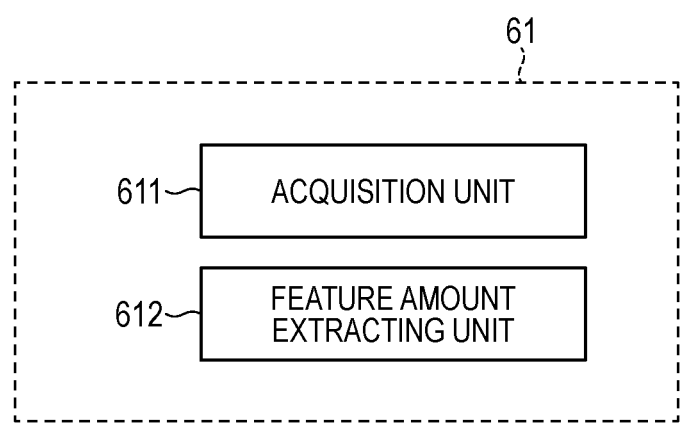
FIG. 13 is a functional block diagram of an information processing device according to a second example embodiment.

FIG. 13 is a functional block diagram of the information processing device 61 according to the second example embodiment. The information processing device 61 includes an acquisition unit 611 and a feature amount extracting unit 612. The acquisition unit 611 acquires load information based on a load applied to a load measurement device from a sole of a user. The feature amount extracting unit 612 extracts a feature amount indicating weight of the user by time-integrating time series data included in the load information.

According to the present example embodiment, the information processing device 61 capable of extracting the feature amount of the weight with high accuracy is provided.

Modified Example Embodiments

The present invention is not limited to the example embodiments described above, and may be suitably modified within the scope of the present invention. For example, an example in which a part of the configuration of one example embodiment is added to another example embodiment or an example in which a part of the configuration of one example embodiment is replaced with another example embodiment is also an example embodiment of the present invention.

Although the weight estimation process is performed inside the weight estimation device 1 in the above-described example embodiment, this function may be provided in the information communication terminal 2. In this case, the information communication terminal 2 functions as a weight estimation device.

In the example embodiment described above, the time series data of the load is acquired from the two load measurement devices, but the number and arrangement and the like of the load measurement devices are not limited thereto. For example, the number of load measurement devices may be one or three or more. When there is one load measurement device, the amount of data to be acquired is reduced, so that the amount of data to be processed may be reduced. When the number of load measurement devices is three or more, more information can be acquired, so that the accuracy of estimating the weight may be improved.

In the above-described example embodiment, although the load measurement device is a load cell or the like and acquires a local load on the sole of the user 4, the load measurement device may be configured to acquire a load distribution over a wide range of the sole. For example, the load measurement device may have a configuration in which a large number of load measurement devices are arranged in the shoe 5, or a configuration in which a seat sensor in which a large number of load detecting elements are two-dimensionally arranged is arranged in the shoe 5 may be employed. In these cases, since the time series data of the load distribution of the sole of the user 4 can be acquired, and more information can be acquired, the accuracy of estimating the weight may be improved.

Further, in the configuration in which the load is measured using the seat sensor described above, it is not essential that the seat sensor be arranged in the shoe 5. For example, the weight estimation system of the above-described example embodiment may be modified to include a seat sensor laid on a floor surface, acquire a load distribution of the sole of the user 4 when the user 4 walks on the seat sensor, and estimate the weight from time series data of the load distribution.

A processing method in which a program for operating the configuration of the above-described example embodiments is recorded in a storage medium so as to implement the functions of the above-described example embodiments, the program recorded in the storage medium is read as code, and the program is executed in a computer is also included in the scope of each example embodiment. That is, a computer-readable storage medium is also included in the scope of the example embodiments. Further, not only the storage medium in which the above program is recorded, but also the program itself is included in each example embodiment. In addition, one or more components included in the above-described example embodiments may be a circuit such as an application specific integrated circuit (ASIC), a field programmable gate array (FPGA) configured to implement the functions of each component.

As the storage medium, for example, a floppy (registered trademark) disk, a hard disk, an optical disk, a magneto-optical disk, a compact disk (CD)-ROM, a magnetic tape, a nonvolatile memory card, or a ROM can be used. Further, the scope of each example embodiment is not limited to the case where the processing is executed by the program alone recorded in the storage medium, and a case where the processing is executed by operating on an operating system (OS) in cooperation with the functions of other software and extension board is also included in the scope of each example embodiment.

The service realized by the functions of the above-described example embodiments may be provided to the user in the form of a software as a service (SaaS).

It should be noted that the above-described example embodiments are merely examples of embodying the present invention, and the technical scope of the present invention should not be limitedly interpreted by these. That is, the present invention can be implemented in various forms without departing from the technical idea or the main features thereof.

The whole or part of the example embodiments disclosed above can be described as, but not limited to, the following supplementary notes.

(Supplementary Note 1)
An information processing device comprising:
an acquisition unit configured to acquire load information based on a load applied to a load measurement device from a sole of a user; and
a feature amount extracting unit configured to extract a feature amount indicating weight of the user by time-integrating time series data included in the load information.
(Supplementary Note 2)
The information processing device according to supplementary note 1, wherein the time series data includes a time change in the load in a period corresponding to at least one walking cycle.
(Supplementary Note 3)
The information processing device according to supplementary note 1 or 2,
wherein the acquisition unit acquires first time series data measured by a first load measurement device provided on the sole and second time series data measured by a second load measurement device provided between a toe of the sole and the first load measurement device, and
wherein a feature amount extracting unit extracts the feature amount based on the first time series data and the second time series data.
(Supplementary Note 4)
The information processing device according to supplementary note 3, wherein the feature amount extracting unit extracts the feature amount based on third time series data acquired by adding the first time series data and the second time series data.
(Supplementary Note 5)
The information processing device according to supplementary note 3 or 4,
wherein the first load measurement device is provided between a heel and a Lisfranc joint of a foot of the user, and
wherein the second load measurement device is provided between a toe and the Lisfranc joint.
(Supplementary Note 6)
The information processing device according to any one of supplementary notes 1 to 5, wherein the feature amount extracting unit extracts the feature amount further based on at least one of a peak and a dip included in the time series data.
(Supplementary note 7)
The information processing device according to supplementary note 1 or 2,
wherein the acquisition unit acquires time series data of a load distribution of the sole measured by the load measurement device, and
wherein the feature amount extracting unit extracts the feature amount based on the time series data of the load distribution.
(Supplementary note 8)
A weight estimation device configured to estimate weight of the user based on the feature amount extracted by the information processing device according to any one of supplementary notes 1 to 7.
(Supplementary Note 9)
A weight estimation system comprising:
the information processing device according to any one of supplementary notes 1 to 7;
a weight estimation device configured to estimate weight of the user based on the feature amount; and
the load measurement device.

(Supplementary Note 10)
An information processing method comprising:
acquiring load information based on a load applied to a load measurement device from a sole of a user; and
extracting a feature amount indicating weight of the user by time-integrating time series data included in the load information.
(Supplementary Note 11)
A storage medium storing a program that causes a computer to perform:
acquiring load information based on a load applied to a load measurement device from a sole of a user; and
extracting a feature amount indicating weight of the user by time-integrating time series data included in the load information.

REFERENCE SIGNS LIST 1 weight estimation device
2 information communication terminal
3 server
4 user
5 shoe
6a, 6b load measurement device
7 Lisfranc joint
61 information processing device
101, 201 CPU
102, 202 RAM
103, 203 ROM
104, 204 flash memory
105, 205 communication I/F
106 sensor control device
107 battery
120, 611 acquisition unit
130, 612 feature amount extracting unit
131 time series processing unit
132 walking cycle identification unit
133 feature amount calculation unit
140 weight estimation unit
150 storage unit
160 communication unit
206 input device
207 output device

What is claimed is:
1. An information processing device comprising:
a memory configured to store instructions; and
a processor configured to execute the instructions to:
acquire load information based on a load applied to a load measurement device from a sole of a user; and
identify one walking cycle from time series data included in the load information; and
extract a feature amount indicating weight of the user by time-integrating the time series data included in the load information by an integration interval of the one walking cycle.
2. The information processing device according to claim 1,
wherein first time series data measured by a first load measurement device provided on the sole and second time series data measured by a second load measurement device provided between a toe of the sole and the first load measurement device are acquired, and
wherein the feature amount is extracted based on the first time series data and the second time series data.
3. The information processing device according to claim 2, wherein the feature amount is extracted based on third time series data acquired by adding the first time series data and the second time series data.

4. The information processing device according to claim 2,
wherein the first load measurement device is provided between a heel and a Lisfranc joint of a foot of the user, and
wherein the second load measurement device is provided between a toe and the Lisfranc joint.

5. The information processing device according to claim 1, wherein the feature amount is extracted further based on at least one of a peak and a dip included in the time series data.

6. The information processing device according to claim 1,
wherein time series data of a load distribution of the sole measured by the load measurement device is acquired, and
wherein the feature amount is extracted based on the time series data of the load distribution.

7. A weight estimation device configured to estimate weight of the user based on the feature amount extracted by the information processing device according to claim 1.

8. A weight estimation system comprising:
the information processing device according to claim 1;
a weight estimation device configured to estimate weight of the user based on the feature amount; and
the load measurement device.

9. An information processing method comprising:
acquiring load information based on a load applied to a load measurement device from a sole of a user; and
identifying one walking cycle from time series data included in the load information; and
extracting a feature amount indicating weight of the user by time-integrating the time series data included in the load information by an integration interval of the one walking cycle.

10. A non-transitory storage medium storing a program that causes a computer to perform:
acquiring load information based on a load applied to a load measurement device from a sole of a user; and
identifying one walking cycle from time series data included in the load information; and
extracting a feature amount indicating weight of the user by time-integrating the time series data included in the load information by an integration interval of the one walking cycle.

* * * * *